(12) United States Patent
Friedman et al.

(10) Patent No.: US 8,333,997 B2
(45) Date of Patent: Dec. 18, 2012

(54) COMPOSITIONS FOR SUSTAINED RELEASE OF NITRIC OXIDE, METHODS OF PREPARING SAME AND USES THEREOF

(75) Inventors: Joel M. Friedman, South Orange, NJ (US); Adam Friedman, New York, NY (US); Mahantesh S. Navati, Bronx, NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 485 days.

(21) Appl. No.: 12/227,657

(22) PCT Filed: Jun. 20, 2007

(86) PCT No.: PCT/US2007/014442
§ 371 (c)(1),
(2), (4) Date: Jul. 13, 2009

(87) PCT Pub. No.: WO2007/149520
PCT Pub. Date: Dec. 27, 2007

(65) Prior Publication Data
US 2009/0297634 A1    Dec. 3, 2009

Related U.S. Application Data

(60) Provisional application No. 60/815,481, filed on Jun. 21, 2006.

(51) Int. Cl.
*A61K 33/00*    (2006.01)
*A61K 47/36*    (2006.01)
*C01B 21/24*    (2006.01)
*A01K 59/00*    (2006.01)
*A01N 25/00*    (2006.01)

(52) U.S. Cl. ......... 424/718; 423/405; 514/788; 514/929

(58) Field of Classification Search ................ None
See application file for complete search history.

(56) References Cited

U.S. PATENT DOCUMENTS

| | | | |
|---|---|---|---|
| 5,972,369 | A | 10/1999 | Roorda et al. |
| 5,994,444 | A | 11/1999 | Trescony et al. |
| 7,678,888 | B2 | 3/2010 | Friedman et al. |
| 2005/0069573 | A1 | 3/2005 | Cohn et al. |
| 2005/0079200 | A1 | 4/2005 | Rathenow et al. |
| 2005/0113409 | A1* | 5/2005 | Connor et al. ............. 514/311 |
| 2005/0147758 | A1 | 7/2005 | Mao et al. |
| 2006/0222564 | A1* | 10/2006 | Dale et al. .................. 422/56 |
| 2008/0188836 | A1 | 8/2008 | Weber et al. |
| 2008/0241262 | A1 | 10/2008 | Lee et al. |
| 2009/0140212 | A1 | 6/2009 | Friedman et al. |
| 2011/0250134 | A1 | 10/2011 | Cabrales et al. |

FOREIGN PATENT DOCUMENTS

WO    2010/123547    10/2010

OTHER PUBLICATIONS

Nablo et al. (JACS 2001, 123, 9712-9713).*
Rothrock A R et al., entitled "Synthesis of nitric oxide-releasing gold nanoparticles," J Am Chem Soc.127:9362-3, 2005; E-publ Jun. 8, 2005.
Polizzi M A et al., entitled "Water-soluble nitric oxide-releasing gold nanoparticles," Langmuir, Apr. 24, 2007;23(9):4938-43.
Shin J H et al., entitled "Synthesis of nitric oxide-releasing silica nanoparticles," J Am Chem Soc., 129:4612-9, 2007; E-publ Mar. 22, 2007.
Hetrick E M et al., entitled "Bactericidal efficacy of nitric oxide-releasing silica nanoparticles," ACS Nano, Feb. 2007;2(2):235-46.
Friedman A et al., entitled Sustained release of therapeutic levels of NO from micro- and Nano-vehicles. IN: Nitric Oxide published online May 5, 2006, vol. 14, No. 4, p. 51, Abstract p. 106.
Friedman et al. "Sustained release nitric oxide releasing nanoparticles: Characterization of a novel delivery platform based on nitrite containing hydrogel/glass composites." Nitric Oxide 19 (2008), pp. 12-20.
Martinez et al. "Antimicrobial and healing efficacy of sustained release nitric oxide nanoparticles against *Staphylococcus aureus* skin infection." J Invest Dermatol. Apr. 23, 2009 [Epub ahead of print].
The International Preliminary Report on Patentability for PCT Application No. PCT/US2007/014442.
The Written Opinion of the International Searching Authority for PCT Application No. PCT/US2007/014442.
Shimojima A et al., entitled "Synthesis of Layered Inorganic-Organic Nanocomposite Films from Mono-, Di-, and Trimethoxy(alkyl)silane-Tetramethoxysilane Systems," Chem. Mater, 2001, vol. 13, 3610-3616.

* cited by examiner

*Primary Examiner* — Ernst Arnold
(74) *Attorney, Agent, or Firm* — Rothstein & Ebenstein LLP

(57) ABSTRACT

The invention provides compositions for releasing nitric oxide (NO) comprising a matrix that encapsulates nitric oxide. Nitric oxide is released when the composition is exposed to an aqueous environment. The invention further provides methods of preparing the compositions and uses of the compositions for treating infections and disorders.

32 Claims, 14 Drawing Sheets

US 8,333,997 B2

COMPOSITIONS FOR SUSTAINED RELEASE OF NITRIC OXIDE, METHODS OF PREPARING SAME AND USES THEREOF

CROSS-REFERENCE TO RELATED APPLICATIONS

This application is a U.S. national stage entry under 35 U.S.C. §371 of PCT International Patent Application No. PCT/US2007/014442, filed Jun. 20, 2007, and claims priority to U.S. Provisional Patent Application No. 60/815,481, filed Jun. 21, 2006, the contents of which are incorporated herein by reference in their entirety.

BACKGROUND OF THE INVENTION

Nitric oxide (NO) plays a central role in a number of biological processes such as infection, vasodilation, angiogenesis, and modulation of wound healing (Fang, 1999; Frank et al., 2002; Liew et al., 1991; Rizk et al., 2004; Weller et al., 2001). As an example, a disturbing trend in the treatment of superficial infections is increasing antibiotic resistance among staphylococcal isolates, resulting from current antibiotic pressure. Today, less than 5% of clinical isolates remain sensitive to penicillin (Smith et al., 1999). In the 1980s, methicillin-resistant *S. aureus* (MRSA) emerged as a prominent hospital-based infection stimulating an increase in the use of vancomycin. A 1997 survey by the Center for Disease Control (CDC) showed that the proportion of methicillin-resistant isolates with sensitivity only to vancomycin increased from 22.8% in 1987 to 56.2% in 1997. Conventional antibacterial treatments for wound infection are becoming less effective not only due to the emergence of antibiotic-resistant strains but also due to the avascular nature of extensive wounds. Many virulent bacteria such as the Staphylococci secrete polymeric materials after association to form protective coatings known as biofilms. The biofilm further impedes the activity of the host defenses and standard antibiotic therapy. Together, these confounding factors impede the effect of systemically administered antibiotics (Costerton et al., 2001).

The body naturally combats infection through numerous biological mechanisms. One such mechanism is the production of nitric oxide (NO) (FIG. 11). NO is produced enzymatically by any of three distinct nitric oxide synthases (NOS) via L-arginine conversion. Each isoform differs considerably in its pattern of expression and regulation. The isoforms of NO are synthesized and released by various cells resident in the skin such as nielanocytes, adipocytes, endothelial cells, macrophages, neutrophils, fibroblasts, and keratinocytes (Heck et al., 1992; Ivanova et al., 1997; MacMicking et al., 1997). The chemical reactivity of NO in the living system is diverse and extensive. The electronic make up of NO allows for diverse interactions with numerous molecular agents. Because NO is lipophilic, readily crossing most natural barriers, it can reach most target cells with relative ease (Subczynski et al., 2000). NO can diffuse along its concentration gradient, permitting it to rapidly move from cell to cell independent of receptors and channels. Because of its high reactivity and short half-life, NO action and biological impact is determined by its rate of formation. Furthermore, because NO is rapidly scavenged by hemoglobin, its site of action is typically very local with respect to where it is generated. However, despite the wide spread therapeutic promise of gaseous NO (gNO), a practical gNO delivery system for most potential applications has yet to emerge.

SUMMARY OF THE INVENTION

The present invention provides compositions for releasing nitric oxide (NO). A preferred composition for releasing nitric oxide (NO) comprises nitric oxide encapsulated in a matrix of chitosan, polyethylene glycol (PEG), and tetra-methoxy-ortho-silicate (TMOS). Another preferred composition for releasing nitric oxide (NO) comprises nitric oxide encapsulated in a matrix of trehalose, and non-reducing sugar or starch.

The invention also provides a composition comprising nitrite, reducing sugar, chitosan, polyethylene glycol (PEG) and tetra-methoxy-ortho-silicate (TMOS). The invention further provides a composition comprising nitrite, reducing sugar, chitosan, trehalose, and non-reducing sugar or starch.

The invention further provides methods for preparing a composition for releasing nitric oxide (NO), the methods comprising: (a) admixing nitrite, reducing sugar, chitosan, polyethylene glycol (PEG), and tetra-methoxy-ortho-silicate (TMOS); (b) drying the mixture of step (a) to produce a gel; and (c) heating the gel until the gel is reduced to a powdery solid. The invention also provides methods for preparing a composition for releasing nitric oxide (NO), the methods comprising: (a) admixing nitrite, reducing sugar, chitosan, trehalose, and non-reducing sugar or starch; (b) drying the mixture of step (a) to produce a film; and (c) heating the film to form a glassy film. The invention further provides compositions prepared by the disclosed methods.

In addition, the invention provides methods for treating infections and disorders comprising administering compositions for releasing nitric oxide (NO) to a subject.

Additional objects of the invention will be apparent from the description which follows.

BRIEF DESCRIPTION OF THE DRAWINGS

In FIG. 3A, 2 logs of killing are consistently observed for the different weights after 4 hrs. incubation with the microgels. FIG. 3B extends the assay to the 24 hrs of incubation with the microgels. The killing ranges from 3.25 logs to 5 logs over the given weight range (0.5-0.9 g). X-axis—weight in grams; Y-axis—CFU/ml. microp=microparticles.

DETAILED DESCRIPTION OF THE INVENTION

Figures 1A, 1B:
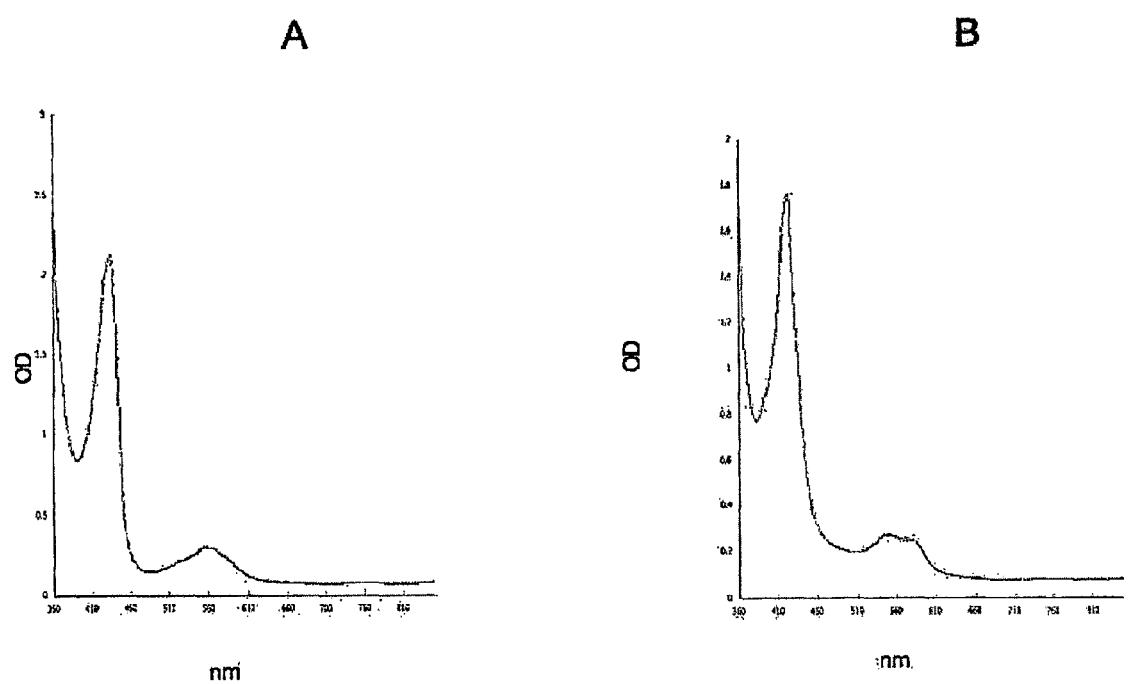
FIGS. 1A-1B. Spectroscopic evidence of nitric oxide release from microgels. This figure demonstrates that the gas released from the dry microgel when added to water is nitric oxide. When the powder is added to water, bubbling is immediately observed. The bubbling persists from days to weeks depending on the amount and composition of the added powder. Absorption changes show the conversion of deoxy myoglobin (spectrum A) to NO ferrous myoglobin (spectrum B) upon introducing the gas released when the microgel derived powder is added into a solution of oxygen free deoxy myoglobin.

The present invention provides compositions for releasing nitric oxide (NO) comprising a matrix that encapsulates nitric oxide. Nitric oxide is released when the composition is exposed to an aqueous environment. As used herein, aqueous environments include moist environments, including for example, the surface of the skin.

A preferred composition for releasing nitric oxide (NO) comprises nitric oxide encapsulated in a matrix of chitosan, polyethylene glycol (PEG), and tetra-methoxy-ortho-silicate (TMOS). Another preferred composition for releasing nitric oxide (NO) comprises nitric oxide encapsulated in a matrix of trehalose, and non-reducing sugar or starch. The composition can further comprises nitrite, reducing sugar, and/or chitosan. Nitric oxide is released when the composition is exposed to an aqueous environment. For example, one preferred composition for releasing nitric oxide (NO) comprises nitrite; reducing sugar; chitosan; polyethylene glycol (PEG); tetra-methoxy-ortho-silicate (TMOS); and nitric oxide encapsulated in a matrix of chitosan, PEG and TMOS; wherein nitric oxide is released when the composition is exposed to an aqueous environment. Another preferred composition for releasing nitric oxide (NO) comprises nitrite; reducing sugar; chitosan; trehalose; a non-reducing sugar or starch; and nitric oxide encapsulated in a matrix of trehalose and the non-reducing sugar or starch; wherein nitric oxide is released when the composition is exposed to an aqueous environment.

The invention also provides a composition comprising nitrite, reducing sugar, chitosan, polyethylene glycol (PEG) and tetra-methoxy-ortho-silicate (TMOS), and a composition comprising nitrite, reducing sugar, chitosan, trehalose, and non-reducing sugar or starch.

As used herein, a "reducing sugar" is a sugar that has a reactive aldehyde or ketone group. The reducing sugar is used to reduce nitrite to nitric oxide. All simple sugars are reducing sugars. Sucrose, a common sugar, is not a reducing sugar.

The invention also provides methods for preparing compositions for releasing nitric oxide (NO), as well as compositions for sustained release of NO prepared by the methods.

One preferred method for preparing a composition for releasing nitric oxide (NO) comprises:

(a) admixing nitrite, reducing sugar, chitosan, polyethylene glycol (PEG), and tetra-methoxy-ortho-silicate (TMOS);

(b) drying the mixture of step (a) to produce a gel; and (c) heating the gel until the gel is reduced to a powdery solid.

The nitrite is reduced to nitric oxide by the reducing sugar, and nitric oxide is encapsulated in the powdery solid. The encapsulated nitric oxide is released when the composition is exposed to an aqueous environment.

The method can further comprises grinding the solid of step (c) to produce particles of a desired size. Preferably, the gel is heated in step (c) to a temperature of 55-70° C., more preferably to about 60° C. Preferably, the gel is heated in step (c) for 24-28 hours.

Another preferred method for preparing a composition for releasing nitric oxide (NO) comprises:

(a) admixing nitrite, reducing sugar, chitosan, trehalose, and non-reducing sugar or starch;

(b) drying the mixture of step (a) to produce a film; and (c) heating the film to form a glassy film.

The nitrite is reduced to nitric oxide by the reducing sugar, and nitric oxide is encapsulated in the glassy film. The encapsulated nitric oxide is released when the composition is exposed to an aqueous environment.

Preferably, the film is heated in step (c) to a temperature of 55-70° C., more preferably to about 65° C. Preferably, the film is heated in step (c) for about 45 minutes.

Preferably, the nitrite is a monovalent or divalent cation salt of nitrite, including for example, one or more of sodium nitrite, calcium nitrite, potassium nitrite, and magnesium nitrite. Preferably, the concentration of nitrite in the composition is 20 nM to about 1 M.

Examples of reducing sugars include one or more of glucose, tagatose, galactose, ribose, fructose, lactose, arabinose, maltose, and maltotriose. Different isomers can be used, for example D-glucose and L-glucose. Preferably, the concentration of reducing sugar in the composition is 20 mg-100 mg of reducing sugar/ml of composition.

Preferably, the non-reducing sugar is sucrose.

Preferably, the total amount of sugar in compositions comprising both reducing and non-reducing sugars is 80-120 mg sugar/ml of composition. Preferably, the ratio of trehalose:non-reducing sugar:reducing sugar is 40-80:10-30:10-30 mg of each in 100 ml of solvent in the composition.

In one preferred composition, the non-reducing sugar is sucrose and the reducing sugar is tagatose. Preferably, trehalose, sucrose and tagatose are present in the composition in a ratio by weight of 3:1:1, ±20%.

Preferably, the chitosan is at least 50% deacetylated. More preferably, the chitosan is at least 80% deacetylated. Most preferably, the chitosan is at least 85% deacetylated. Preferably, the concentration of chitosan in the composition is 0.05 g-1 g chitosan/100 ml of composition. Preferably, chitosan enhances particle stability, controlled release of nitric oxide, and cutaneous penetration.

Preferably, the polyethylene glycol (PEG) has a molecular weight of 200 to 20,000 Daltons and more preferably 400 to 10,000 Daltons. A preferred polyethylene glycol has a molecular weight of 400 Daltons. In another embodiment, the PEG is PEG 5,000 to PEG 10,000. PEGs of various molecular weights, conjugated to various groups, can be obtained commercially, for example from Nektar Therapeutics, Huntsville, Ala. Preferably, the concentration of polyethylene glycol (PEG) in the composition is 1-5 ml of PEG/24 ml of composition.

Preferably, the concentration of tetra-methoxy-ortho-silicate (TMOS) in the composition is 0.5 ml-5 ml of TMOS/24 ml of composition.

Preferably, the starch is one or more of inulin, dextran or penta starch.

In one preferred composition for releasing nitric oxide, the composition is in the form of particles having a diameter of 0.1 μm to 1,000 μm or a diameter of 0.09 μM to 100 μm.

Preferably, the compositions for releasing NO are non-toxic, nonimmunogenic and biodegradable.

The compositions for releasing NO described herein can be delivered to a subject by a variety of routes of delivery, including but not limited to percutaneous, inhalation, oral, local injection and intravenous introduction. The compositions can be incorporated, for example, in a cream, ointment, transdermal patch, implantable biomedical device, facial patch or facial scrub. The facial scrub is a cream based product, which can further comprises abrasive particles. The facial scrub or facial pad can comprise antimicrobial nanoparticles. Preferably, the antimicrobial nanoparticles have an average diameter of less than about 500 nm, more preferably less than about 250 nm, and most preferably less than about 150 nm.

The invention provides a method for controlling delivery of nitric oxide to a subject comprising applying to the subject any of the compositions for releasing NO described herein.

The invention also provides methods of treating an infection in a subject comprising administering to the subject an amount of any of the compositions for releasing NO described herein effective to treat the infection. The term "infection" is used to include infections that produce an infectious disease. The infection diseases include communicable diseases and contagious diseases. As used herein, the term "treat" an infection means to eliminate the infection, to reduce the size of the infection, to prevent the infection from spreading in the subject, or to reduce the further spread of the infection in the subject.

The infection can be, for example, a bacterial, viral, fungal or parasitic infection. The bacterial infection can be a Staphylococcal infection. The bacterial infection can be caused, for example, by a bacterium selected from the group consisting of *S. aureus, B. circulans, B. cereus, E. coli, P. vulgaris, P. acnes, S. pyognenes, S. enterica, V. anguillarum, K. pneumoniae, P. piscicida, P. aeruginosa, A. tumefaciens, C. micgiganence, A. mali, E. chrysanthemi, X. campestris, C. diplodiello, P. piricola, M. tuberculosis*, and *M. ulcerans*. The fungal infection can be caused, for example, by a fungus selected from the group consisting of *T. equinum, C. Albicans, F. oxysporum, R. solani, B. cinerea*, and *A. flavus*. The viral infection can be caused, for example, by a virus selected from the group consisting of *M. contagiosum*, Rota, Papilloma, Parvo, and Varicella. The parasite infection can be caused, for example, by a parasite of the genus *Plasmodium, Leishmania, Schistosoma, Austrobilharzia, Heterobilharzia, Ornithobilharzia* or *Crypiosporidium*, for example *P. falciparum*.

The invention also provides methods of promoting angiogenesis, vasodilation, wound healing, or hair growth in a subject comprising administering to the subject an amount of any of the compositions for releasing NO described herein effective to promote angiogenesis, vasodilation, wound healing, or hair growth.

The invention further provides methods of treating a disorder in a subject comprising administering to the subject an amount of any of the compositions for releasing NO described herein effective to treat the disorder, wherein the disorder is selected from the group consisting of peripheral vascular disease, erectile dysfunction, scleroderma and sickle cell anemia. The term "treat" a disorder means to reduce or eliminate a sign or symptom of the disorder, to stabilize the disorder, or to reduce further progression of the disorder.

The invention is illustrated in the following Experimental Details section, which is set forth to aid in the understanding of the invention, and should not be construed to limit in any way the scope of the invention as defined in the claims that follow thereafter.

EXPERIMENTAL DETAILS

I. Overview

The present study describes platforms and methods for delivering gaseous NO (gNO), and examples of their uses. The platform for preparing the NO releasing materials is based on the reduction of nitrite to NO using reducing sugars as a source of thermal electrons. This approach allows for control of the rate, duration, and amount of NO released once the dry glassy formulation is exposed to an aqueous environment.

II. Examples of Preparation of Compositions for Sustained Release of Nitric Oxide (NO)

Two flexible protocols have been developed for preparation of sustained release NO. There are two elements to both of the protocols. First is the generation of NO from nitrite. The second is the storage of NO in, and sustained release from, a matrix associated with the different protocols. In both cases, heat initiated conversion of nitrite to NO mediated through a reducing sugar such as glucose, tagatose or fructose is the source of the NO. The matrix for the NO is in one case derived from polyethylene glycol (PEG), chitosan and tetra-methoxy-ortho-silicate (TMOS). In the second case, the matrix is derived from trehalose and sucrose, which by themselves do not facilitate the formation of NO from nitrite. The combination of trehalose with sucrose is effective in that together they form a glassy matrix without the complication of crystal formation. Trehalose by itself tends to form crystals (as opposed to a glassy matrix which is needed to store the generated NO) if the concentration and temperature are not carefully controlled. The addition of sucrose eliminates that complication. Hence any combination of sugars and starches (e.g. inulin) that form stable glasses are suitable for the second protocol. Different mixtures of sugars and starches should yield glasses with varying stabilities and storage/release capabilities.

Protocol A: The protocol begins with the sonication of tetramethoxy-ortho silicate (TMOS). For every 1 ml of TMOS, 112 microliters of HCl (0.2 mM) and 121 miroliters of deionized (di.) water are added. Sonicate the mixture of TMOS/HCl/water in a cooled water bath×40 minutes. Following sonication, place in ice until use.

To create the gel, add the following contents together at the following ratios: Glucose (20 mg/ml of total composition), Chitosan 0.05% (1 ml:24 ml of total composition): polyethylene glycol (PEG) 400 (1 ml:24 ml of total composition): sonicated TMOS (1 ml:12 ml of total composition): $NaNO_2$ dissolved in di. water (5 ml:6 ml). Note: The sonicated TMOS is added last to the mixture. The concentration of stock $NaNO_2$ for gel preparation can vary depending on the desired amount of NO to be released from the gel. Once TMOS is added, stir and allow time to harden into a gel (several hours). The resulting block is then heated (55-70° C.) for several hours until the gel is reduced to a powdery solid. The heating is needed to generate the glassy particles and cause thermal reduction of the nitrite to NO by the glucose. The resulting material can be ground to generate particles of varying sizes. The use of a ball mill should produce particles on the 0.5 micron size. The powder releases NO when exposed to moisture or when mixed in an aqueous solution. The release is sustained over a period many days to over a month depending on the relative composition of the gel.

Protocol B: Glasses are prepared by drying solutions of trehalose: sucrose: tagatose (60 mg:20 mg:20 mg) in 2 mM $NaNO_2$ in distilled water that also contains 40 mg of dissolved chitosan.

The samples are dried as thin films using a drying chamber maintained at ambient temperatures. The resulting dry films are pealed off and heated to 65° C. for 45 min. Nitric oxide bubbles are observed on the surface of the glass and when added to water release a stream of NO bubble as the particles dissolve.

III. Sustained Release Nitric Oxide Microgels: Therapeutic Efficacy Against *Staphylococcus Aureus*

Based on data demonstrating that NO exhibits potent antimicrobial properties at concentrations above 160 ppm in a dose-response study on *S. aureus* (Ghaffari et al., 2005), the nitrite content of the present microgels was hypothesized to be sufficient to generate therapeutic levels of releasable NO above the bactericidal threshold. The present study demonstrates the efficacy of these materials with respect to killing of *S. aureus* and indicates the usefulness of this sustained release approach as an anti-microbial therapy.

Methods and Materials

Materials. Tetra-methoxy-ortho-silicate (TMOS), D-Glucose, Sodium Nitrite, Polyethylene Glycol (PEG) 400, Chitosan>85% deacytelated, Hydrochloric Acid, Sodium Phosphate, LB Agar, Tryptic Soy Broth.

TMOS Sonication Protocol. 560 μL of HCl are added to 605 μL of dionized water. Following which, 5 ml of TMOS are added to the HCl—$H_2O$ mixture and immediately sonicated for 45 minutes in a cool water bath. Once completed, the now sonicated TMOS is placed on ice.

Hydrogel Synthesis. Sodium Nitrite is dissolved into 50 mM Phosphate Buffer pH 7.5. The relative amounts of sodium nitrite and phosphate Buffer can be varied depending on the desired molarity of the encapsulated Nitrite. D-Glucose is added at a ratio of 20 mg glucose/ml of final volume. Once completely dissolved, PEG 400 is added at a ratio of 1 ml PEG/20 ml Phosphate Buffer. Chitosan 0.05% is added at a ratio of 1 ml Chitosan/20 ml Phosphate buffer. Stir accordingly. The previously sonicated TMOS is pipetted in at a ratio of 2 ml TMOS/20 ml Phosphate buffer. It is stirred immediately and set aside. The resulting mixture will solidify within 10-20 minutes. The resulting gel is initially dried under vacuum suction.

Preparation of Encapsulated gNO. Crush resulting Hydrogel in an open air container. Place in a convection oven at 60° C. and leave until the gel has reduced into a hard, white, crystalline structure (24-48 hrs). If the crystals have taken on a brown discoloration, the glucose has caramelized and the gel should be discarded. Once dry, crush and mix with a mortar and pestel until a fine white powder is produced. Place in a planetary ball mill for 60 minutes at a speed of 140 rpm.

CFU assay. *S. aureus* was grown under aerobic conditions in Tryptic Soy Broth for 12 hours and collected in mid-log phase. The bacteria were washed three times with the TSB and enumerated by OD unit at 600 nm. Various dry weights and concentrations of nitrite free microgels and nitrite encapsulated microgels were incubated with $2 \times 10^{-8}$ bacteria in a final volume of 3 ml at 37° C. for varying times including 4, 6, 7, 8, 16, 24, 36, and 72 hours. After incubation, 10-fold dilutions were prepared and plated on solid media comprised of LB Agar. Plates were incubated for 24 hours at 37° C. under aerobic conditions, then individual colonies were counted and the number of CFU was tabulated.

Antibiotic. The effect of Mupirocin against *S. aureus* was determined with a qualitative CFU Assay. This involved adding varying μL volumes of 1 mM Mupirocin to *S aureus* liquid culture to a final volume of 3 ml in order to achieve desired therapeutic μM concentrations. Following incubation, 10 μL of each sample were added to LB agar plates for incubation and subsequent quantification of colony growth.

Results

Release of gNO from microgels. Upon adding the dry heated microgel derived powder to water, the formation of bubbles was immediately apparent. The bubbling persists from days to weeks depending on the composition of a given amount of the added powder. No such bubble formation was observed when nitrite was omitted from the preparative formulation. That the gas released from the dry microgel when added to water is nitric oxide is readily demonstrated using spectroscopic means. Absorption changes depicted in FIG. 1 show the conversion of deoxymyoglobin (spectrum A) to the ferrous NO derivative of myoglobin (spectrum B) upon introducing the gas released when the microgel derived powder is added into a separate solution of oxygen-free deoxymyoglobin. The vessel containing the bubbling sample was connected via a nitrogen purged tube to a second vessel containing deoxygenated myoglobin.

Figure 2:
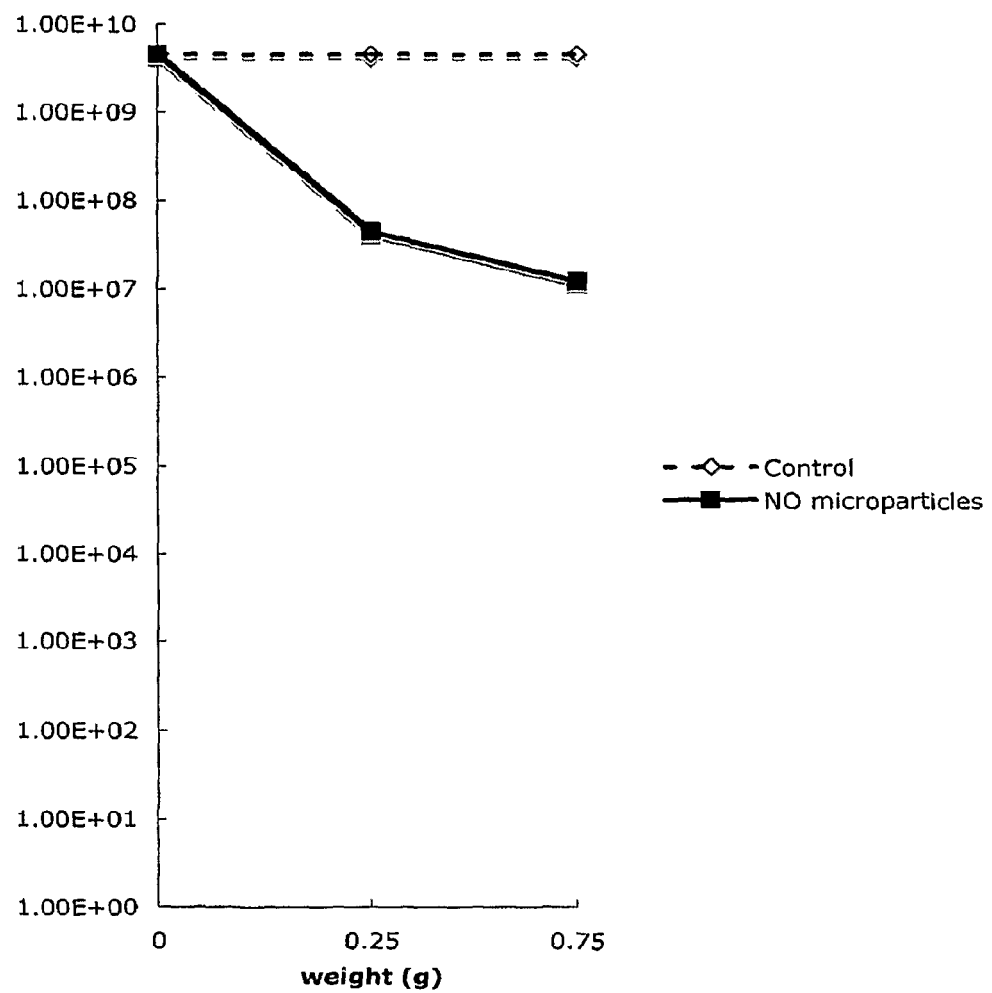
FIG. 2. Killing effectiveness as a function of increasing dry weight of NO containing microgels. Increased killing is noted with increasing dry weight added to 3 ml of *S. aureus* liquid culture, $2\times10^{-8}$ bacteria/ml, following 4 hrs incubation. Results demonstrate 2 logs of killing at the highest weight, with no killing seen by the control (nitrite-free microgel powder) added at the same weight as the highest weight test sample. Y-axis—CFU/ml.

Anti-staphylococcal activity of Nitric Oxide releasing microparticles. FIG. 2 shows the killing effectiveness as a function of increasing dry weight of NO containing microgels added to 3 ml of *S. aureus* liquid culture, $2 \times 10^{-8}$ bacteria/ml, following 4 hrs incubation. Results demonstrate 2 logs of killing at the highest weight, with no killing seen by the control (nitrite-free microgel powder) added at the same weight as the highest weight test sample.

Figure 3A:
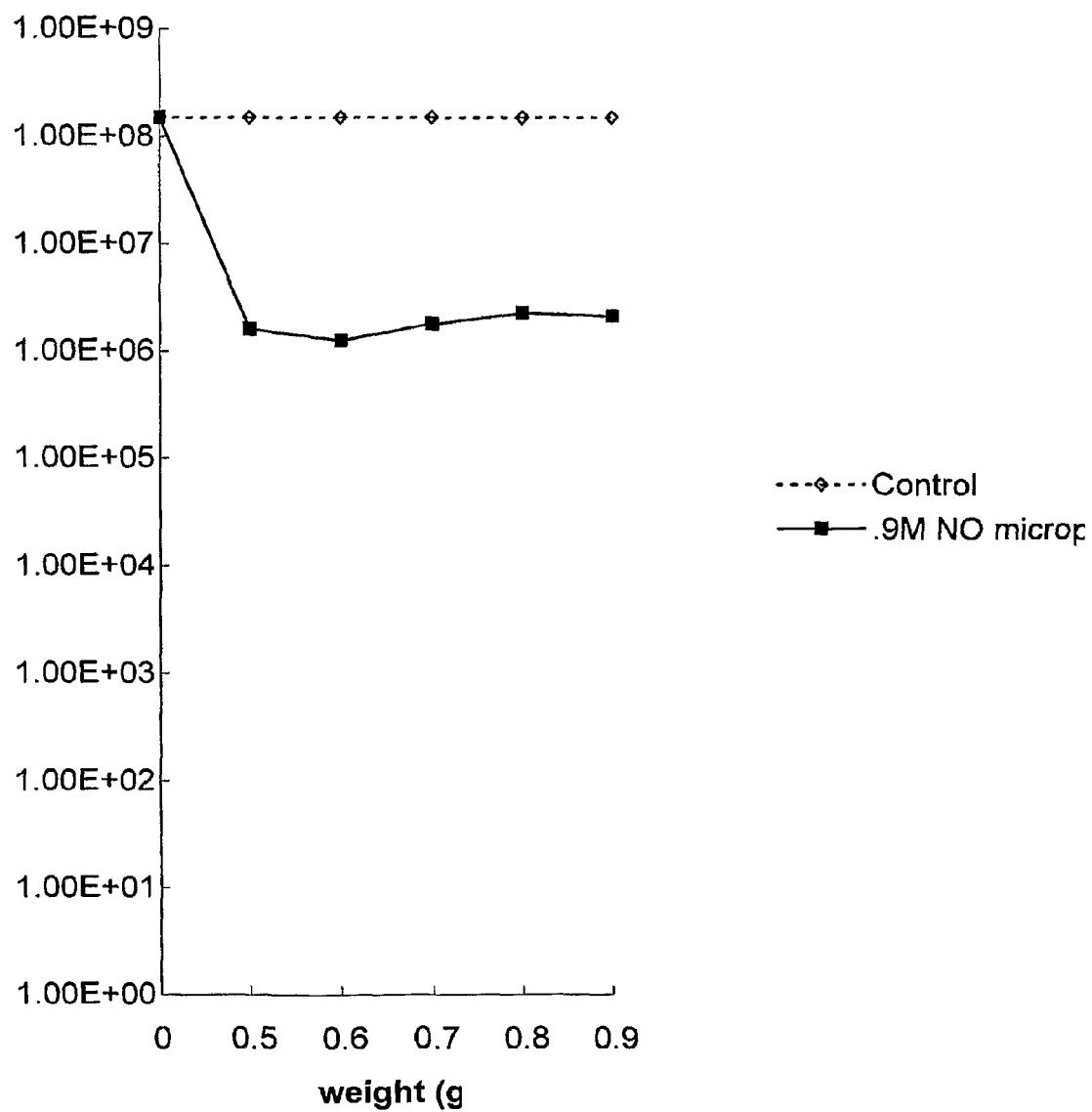
FIGS. 3A-3B. Killing effectiveness of the microgel powder after 4 hrs (A) and 24 hrs (B) as a function of weight of added powder. These two CFU assays represent increasing weights (g) of NO microgels added to 3 ml of *S. aureus* liquid culture, $2\times10^{-8}$ bacteria/ml over two time points.
Figure 3B:
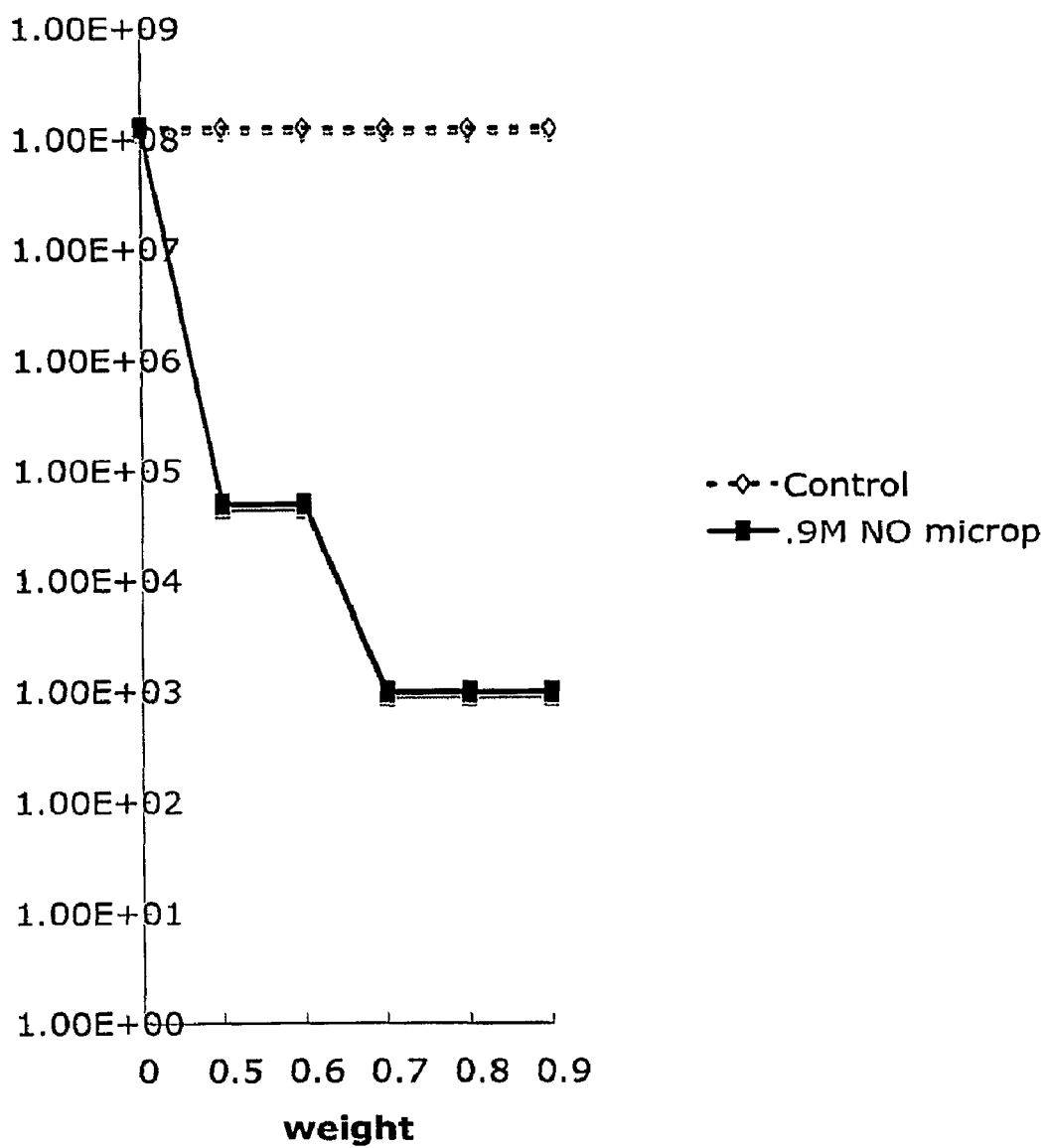

FIG. 3 demonstrates the effectiveness of the microgel powder after 4 hrs and 24 hrs as a function weight of added powder. These two CFU assays represent increasing weights (g) of NO microgels added to 3 ml of *S. aureus* liquid culture, $2\times10^{-8}$ bacteria/ml over two time points. FIG. 3A evaluates the killing impact after 4 hours incubation with the microgels. 2 logs of killing are consistently observed for the different weights. FIG. 3B extends the assay to 24 hours of incubation with the microgels. The killing ranges from 3.25 logs to 5 logs over the given weight range (0.5-0.9 g).

Figure 4A:
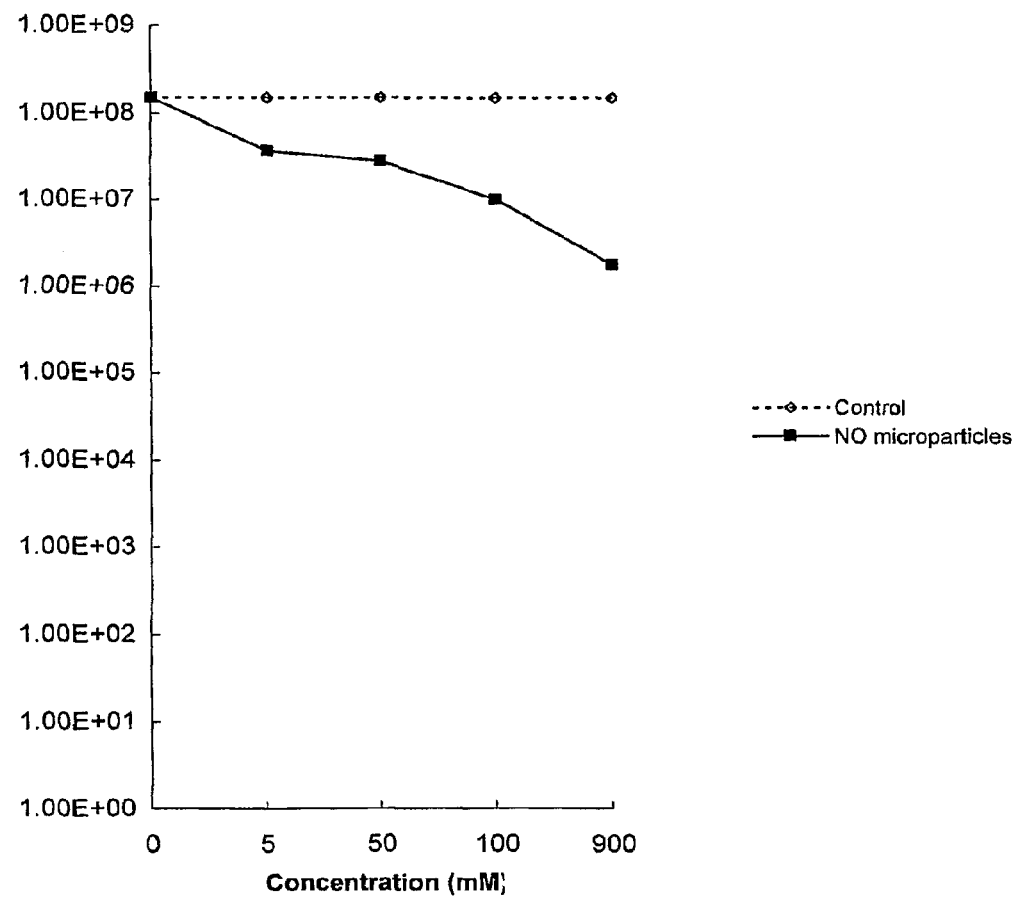
FIGS. 4A-4B. Killing effectiveness of the microgel powder after 4 hrs (A) and 24 hrs (B) as a function of weight of nitrite added to the initial microgel formulation. All of the samples have the same amount of added powder but in each case the initial nitrite content is different. X-axis—concentration (mM); Y-axis—CFU/ml.
Figure 4B:
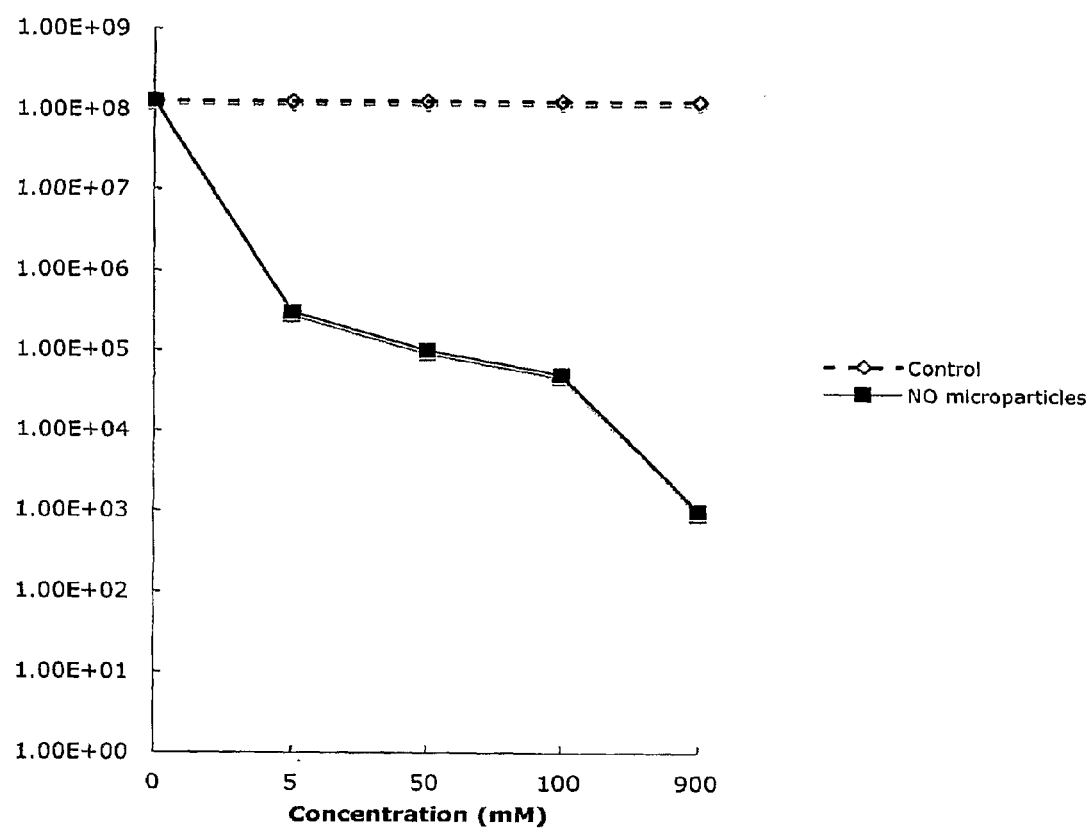

FIG. 4 shows that for an assay to which 0.7 g of powder are added, varying the nitrite concentration (5 mM-900 mM) within the microgel formulation has a significant influence on the extent of *S. aureus* killing both at the 4 and 24 hour incubation points. FIG. 4A shows that at the 4 hour point, there is a little over one and half log variation between the low and high levels of added nitrite. FIG. 4B shows that for each preparation there is a significant increase in killing at 24 hours compared to the corresponding levels at 4 hours. The nitrite concentration dependence at 24 hours spans a slightly greater range than at 4 hours.

Figure 5:
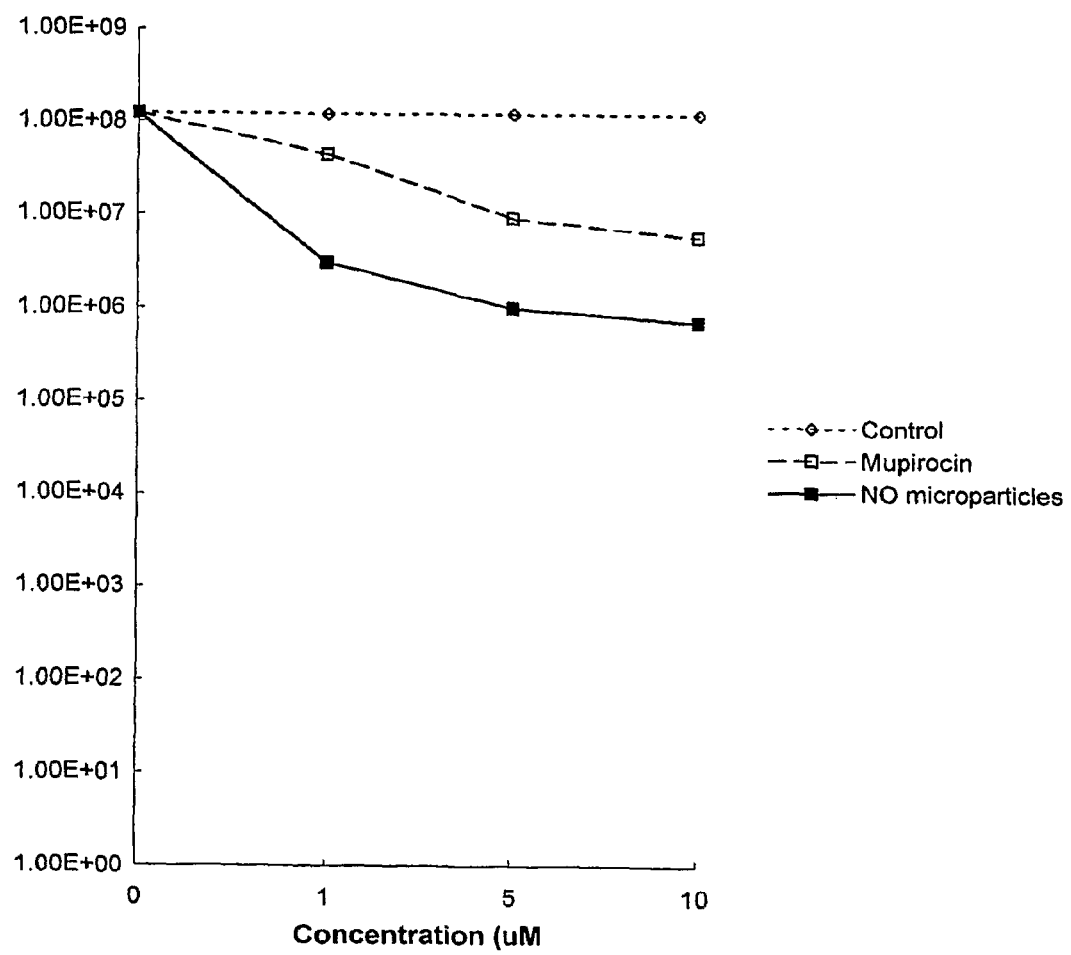
FIG. 5. Particle Efficacy in Comparison to the Gold Standard Mupirocin. A comparison of killing efficacy after 8 hours incubation between the microgel powder and Mupirocin, the gold standard of treatment. Data resulting from a comparison between corresponding concentrations of Mupriocin and the nitrite content of the NO microparticles following eight hours of incubation with each therapeutic reveal a 1 log difference in killing efficacy in favor of the NO microparticles, demonstrating a dose modification factor of 10 at the highest concentration. X-axis—concentration ($\mu M$); Y-axis—CFU/ml.

FIG. 5 is a comparison of killing efficacy after 8 hours incubation between the microgel powder and Mupirocin, the gold standard of Impetigo treatment. Previous studies (Alou et al., 2004; Gisby et al., 2000) have documented efficacious concentration ranges (25-256 mg/l) of Mupirocin against both Methicillin sensitive and Methicillin resistant species. The data resulting from a comparison between corresponding concentrations of Mupirocin and the nitrite content of the NO microparticles following eight hours of incubation with each therapeutic reveal a 1 log difference in killing efficacy in favor of the NO microparticles, demonstrating a dose modification factor of 10 at the highest concentration.

Figures 6A, 6B:
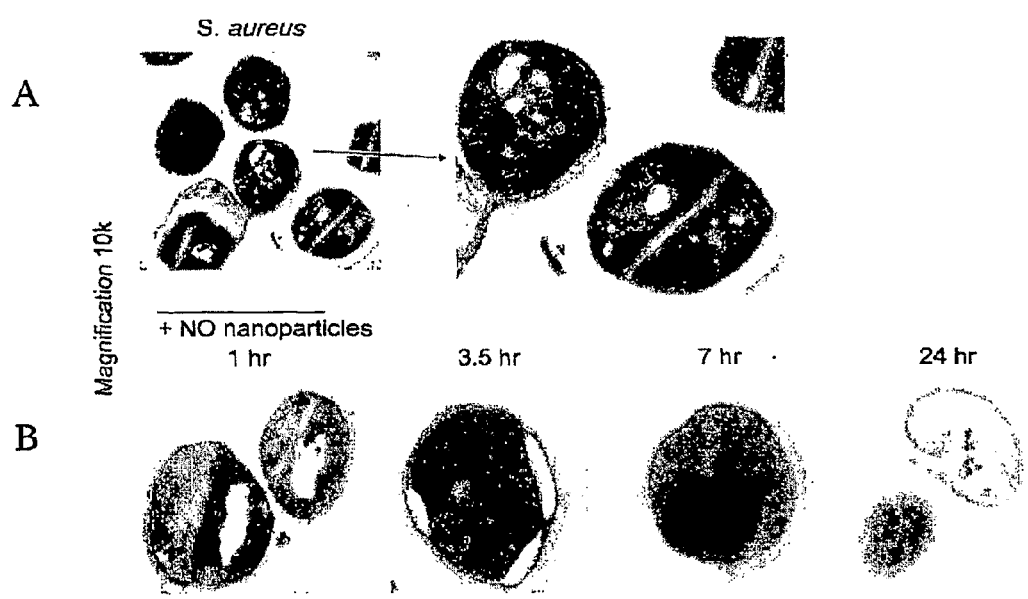
FIGS. 6A-6B. Time scaled evaluation of NO microparticles on Transmission Electron Microscopy. An evaluation of NO microparticle efficacy over time points (t=0, 1, 3.5, 7, and 24 hrs). (A) Normal cells displaying regular cell separation by a cross wall surrounding a highly contrasting splitting system. (B) Increasing destruction of cell wall architecture, edema, and finally cell lysis.

Biological mechanism of NO microparticles. To determine the biological mechanism employed in the killing of *S. aureus* by the microparticles, bacteria that had been treated with NO microparticles were examined using transmission electron microscopy (TEM). TEM micrographs of untreated *S. aureus* illustrate the bacterium's normal pleomorphic structure (FIG. 6A). The untreated *S. aureus* had normal cells displaying regular cell separation by a cross wall surrounding a highly contrasting splitting system with very little cell lysis observed. In contrast, after incubation with NO microparticles, *S. aureus* lost the integrity of this surface architecture with deficiencies of the cell wall (spheroplasts) after only 1 hour of incubation with the NO microparticles (FIG. 6B). In addition, a wider, likely edematous, space inside of the cell wall was observed by 3.5 hours of incubation, further suggesting its disruption as well as peripheral clumping of nuclear material within the cell. By 24 hrs incubation, complete cell lysis was observed. In whole, these images reveal that NO microparticles perturb the surface integrity of *S. aureus* in a manner that may make it porous, suggesting that this is the likely mechanism by which it kill this organism.

Figure 7:
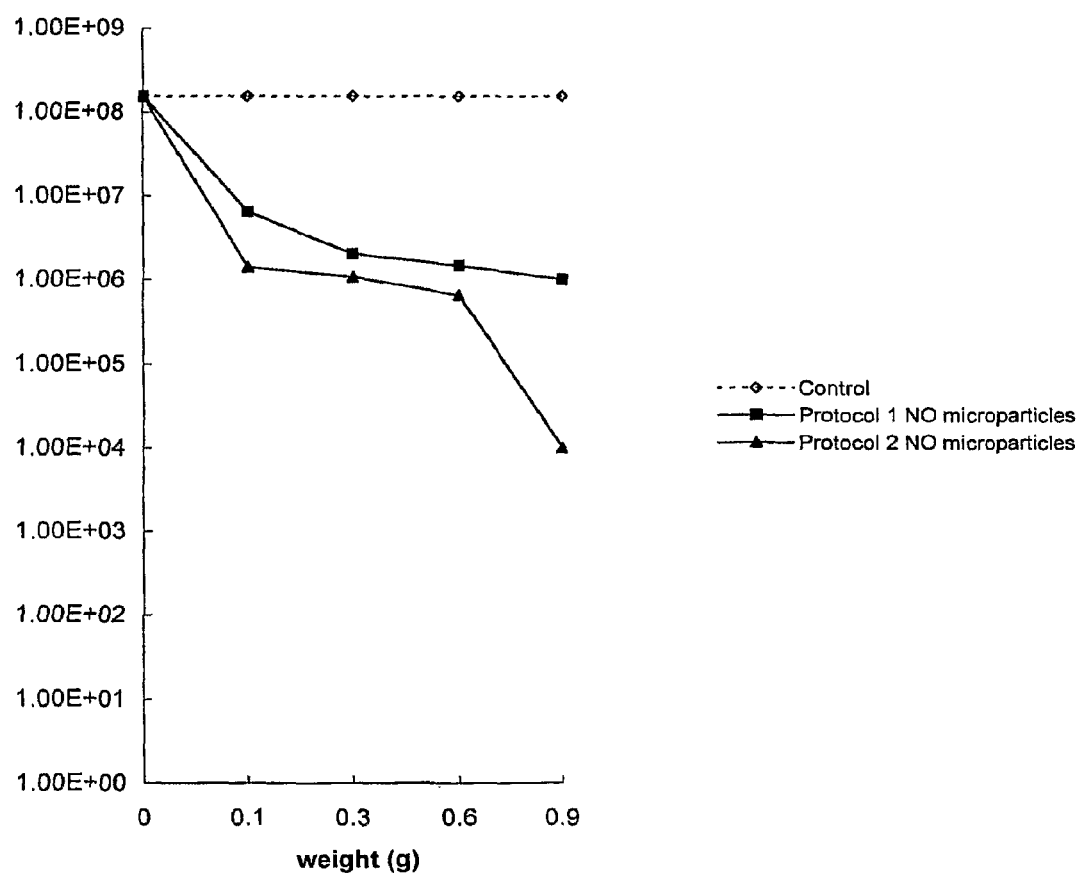
FIG. 7. Killing efficacy for two different preparative microgel protocols. The two protocols differ only in the amount of gel precursor (tetramethoxy silane) contained in the formulation. As the dose (in weight(g)) increases, there is a parallel increase in killing impact between the two preparations. However, Protocol 2 demonstrates a greater killing impact throughout, the maximum impact at 0.9 g with 4 logs of killing following 6 hours of incubation with the *S. aureus* liquid culture. At this weight and time point, Protocol 1 only demonstrates a maximum of 2.15 logs of killing. The control (open diamond) demonstrated no killing impact. X-axis—weight in grams; Y-axis—CFU/ml.

Controlled release of NO from the microparticles. FIG. 7 shows the killing efficacy for two different preparative microgel protocols that differ only in the amount of gel precursor (tetramethoxy silane) contained in the formulation and not in the amount of added nitrite. As the dose (weight(g)) of added powder) increases, there is a parallel increase in killing impact between the two preparations. However, Protocol 2 (closed triangle) demonstrates a greater killing impact throughout, the maximum impact at 0.9 g with 4 logs of killing following 6 hours of incubation with the *S. aureus* liquid culture. At this weight and time point, Protocol 1 (closed squares) only demonstrates a maximum of 2.15 logs of killing. The control demonstrated no killing impact.

The mechanism of bactericidal impact of the micro/nanoparticles was evaluated using TEM imaging, which demonstrated microparticle induced disruption of the bacterial cellular membranes.

IV. Controlled Release Nitric Oxide Nanoparticles: Efficacy of an Antibiotic Alternative Against *P. Falciparum*

Figure 8:
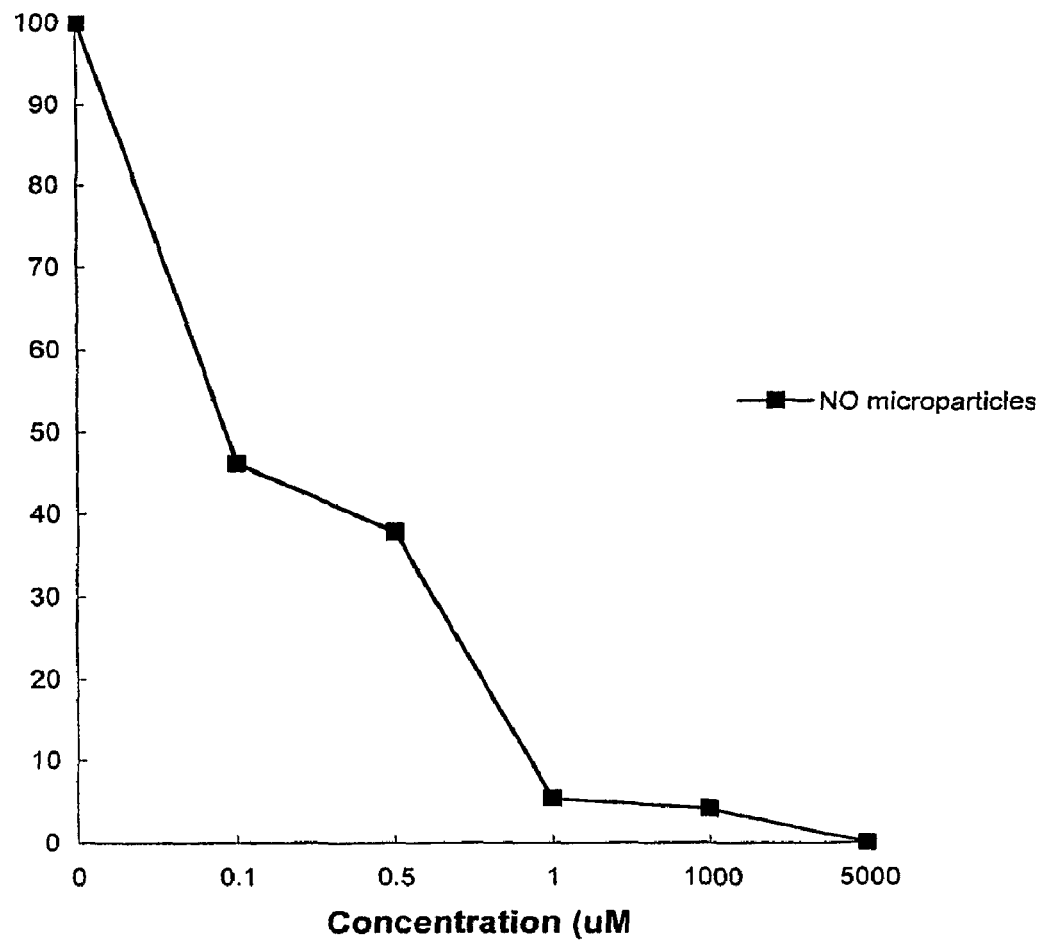
FIG. 8. Percent survival curve for malaria causing parasite *P. falciparum* showing the influence of increasing concentrations of nitrite (ranging from 0.1 $\mu M$ to 5 mM) contained within a fixed weight (25 mg/ml) of added microgel powder. At the lowest concentration, the percent survival is under the 50% mark, demonstrating the killing impact against *P. falciparum*. X-axis—concentration ($\mu M$); Y-axis—% survival.

The efficacy of the nitric oxide releasing compositions was also demonstrated against the malaria causing parasite *Plasmodium falciparum*. FIG. 8 shows the percent survival curve for *P. falciparum* showing the influence of increasing concentrations of nitrite (ranging from 0.1 µM to 5 mM) contained within a fixed weight (25 mg/ml) of added microgel powder. At the lowest concentration, the percent survival is under the 50% mark, demonstrating the killing impact against *P. falciparum*.

Figure 9:
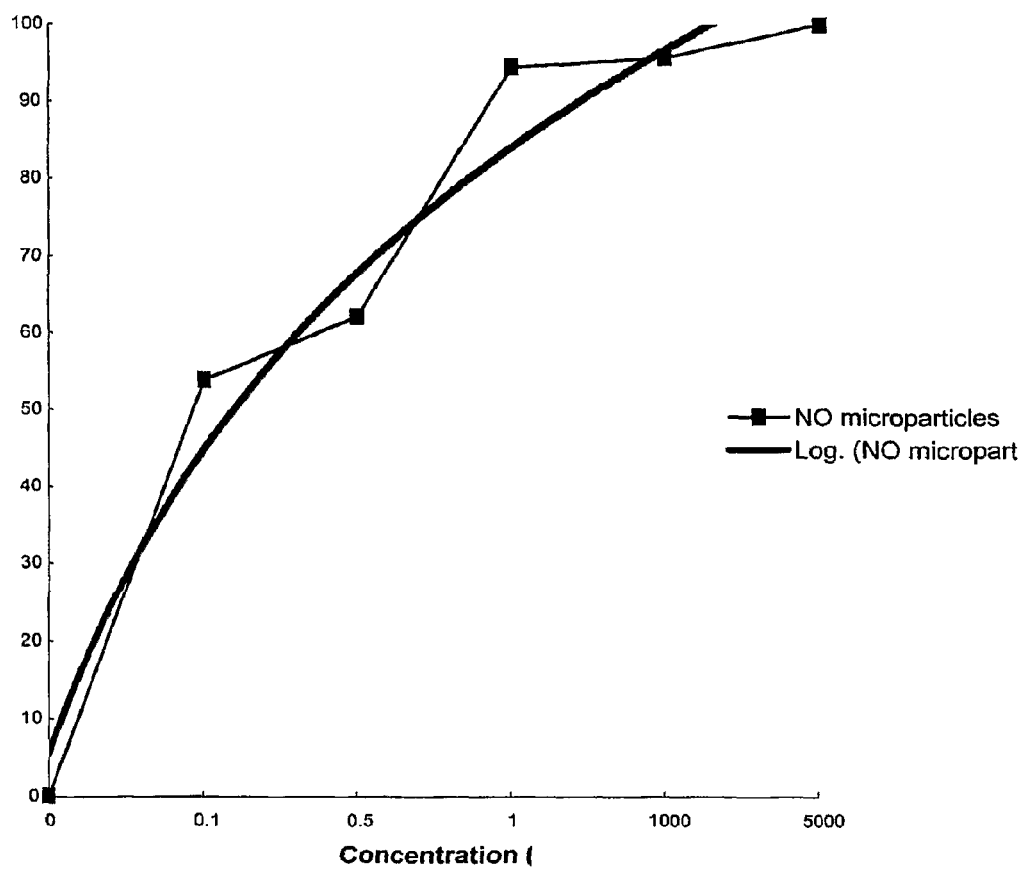
FIG. 9. Efficacy curve showing nitrite concentration dependent impact of the NO microparticles against *P. falciparum* (as in FIG. 8). At the lowest concentration, 0.1 $\mu M$, passes the 50% efficacy mark. X-axis—concentration ($\mu M$); Y-axis—Efficacy. micropart=microparticles.
Figure 10:
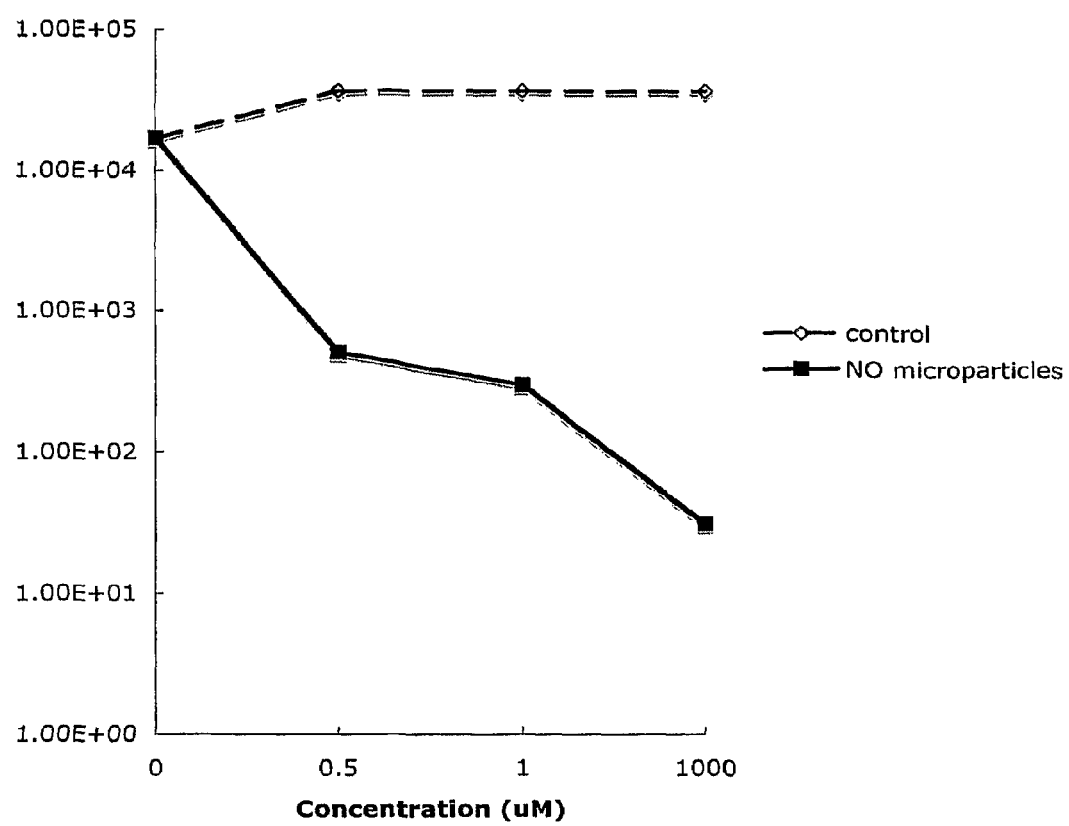
FIG. 10. This measures the dose dependent efficacy of increasing concentrations of initial nitrite encapsulated in the microparticles against *P. falciparum* on a logarithmic scale. X-axis—concentration ($\mu M$); Y-axis$\mu$CFU/ml.
Figure 11:
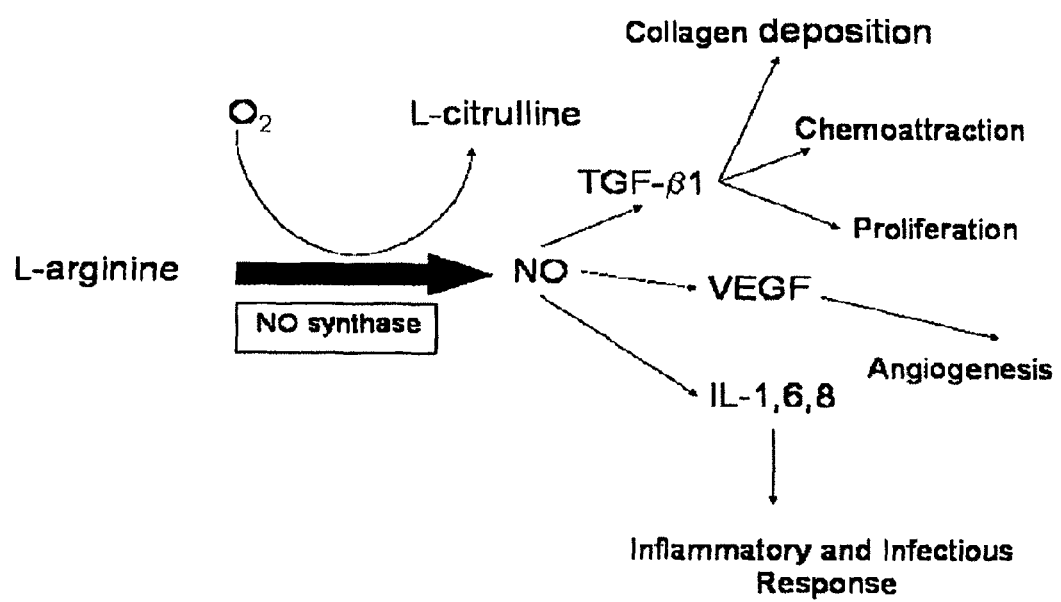
FIG. 11. Scheme of in vivo production and biological roles of nitric oxide (NO).

FIG. 9 plots the efficacy curve showing the nitrite concentration dependent impact of the NO microparticles against *P. falciparum* (as in FIG. 8). At the lowest concentration, 0.1 µM, passes the 50% efficacy mark. FIG. 10 measures the dose dependent efficacy of increasing concentrations of initial nitrite encapsulated in the microparticles against *P. falciparum* on a logarithmic scale.

It has been observed that patients suffering from malaria live in a hypoargenmic state. L-arginine is the known precursor for NO. It is therefore believed that such patients have reduced levels of NO. The present studies have demonstrated the efficacy of the NO microgels against *P. falcirpum*.

V. Sustained Release of Nitric Oxide (NO) from Powder Formulations

Figure 12:
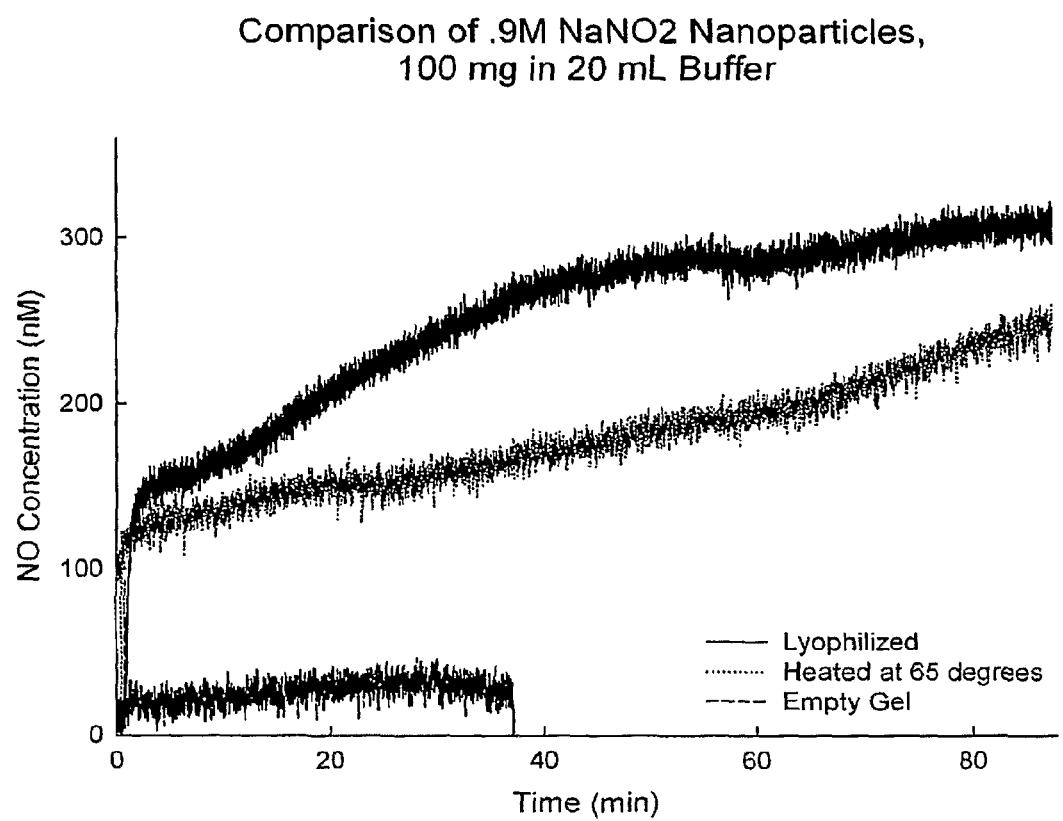
FIG. 12. Sustained release of nitric oxide (NO) from powder formulation. NO release from a control sample (bottom trace) that contains no added nitrite (the source of NO) and nitrite containing samples that were prepared using either freeze drying without heating (lyophilization) or heating as methods for drying the samples.

The rates, amounts and duration of nitric oxide (NO) release from powder formulations were characterized when 100 mg of powder is added to 20 ml of buffered water. NO detection was achieved using an electrochemical detection method (Apollo 4000 detector with a ISO-NOP nitric oxide sensor probe). FIG. 12 shows typical profiles for NO release from a control sample (bottom trace) that contains no added nitrite (the source of NO) and nitrite containing samples that were prepared using either just freeze drying without heating (lyophilization) or heating as methods for drying the samples. Continued measurements over a period of weeks indicate that NO release continues over this period. The preparations yield 0.05-0.1 nanomoles of NO per mg of constant release for samples prepared with 0.9 M nitrite in the starting formulation. A typical formulation consists of the following: 60 mL Sodium Nitrite solution in deionized water (0.9M); Glucose, to make 40 mg/mL final solution concentration (i.e. out of 72 mL); 6 mL hydrolyzed TMOS; 3 mL PEG 400, 3 mL Chitosan, 5%=72 mL total starting solution.

The scientific literature indicates that localized concentrations in the range of 100's of nM of NO are sufficient to produce substantial therapeutic effects without any obvious negative side effects. These levels are easily obtainable using powder formulations described herein.

The inclusion of chitosan was found to be essential for slow sustained release. Without chitosan, NO release is initially rapid but drops off within an hour.

It was also found that PEG prevents aggregation of the particles when dissolved in water. The literature indicates that larger PEGs are more effective in preventing aggregation. Larger PEGs were found to spontaneously incorporate into the particles when suspended in solution resulting in dramatic decrease in particle aggregation. The inclusion of larger PEG molecules (PEG 5000 to 10,000) should yield particles suitable for infusion.

VI. Prophetic Uses for Compositions Providing Controlled Release of Nitric Oxide Topical Antimicrobial—In addition to the results presented herein with respect to *S. aureus*, in vitro studies have demonstrated NO has significant antibacterial and antiviral properties, especially with microbes involved in superficial infections, such as *Molluscum contagiosum*.

Wound healing—Both the vasodilatory effects and sterilizing properties of NO allow for the NO microgels to serve as potent wound healing accelerants. Furthermore, NO is known to advance wound healing from the inflammatory stage to re-epitheliatzation stage. This suggests yet another mechanism of action by which these NO microparticles have potential efficacy. The benefits of hastened and sterile wound healing extend from workplace trauma to surgical recovery. There is the potential that NO releasing compositions could be added to formulations used to limit trauma-induced bleeding.

Hair Growth—Minoxidil has been used for years as a stimulant for hair growth. The result of administration is increased blood flow to the scalp, resulting in hair growth. Similarly, NO is known for its vasodilatory effects on arteries, arterioles, veins and venules. Therefore, the application of the NO microgels to the scalp should also result in hair growth.

Sickle Cell Anemia Crisis—The mechanism of hydroxyurea, a commonly used treatment in sicklers, is not entirely known, though it is hypothesized that it prevents red blood cells (RBCs) from forming their deoxygenated "T" state conformation, thus preventing sickling of the cells. Constant slow administration of a controlled release NO from sustained release patches could be a means of heading off sickle cell crisis. The released NO would bind to the hemoglobin in RBCs, which would favor "R" state conformation which does not sickle.

Erectile dysfunction—Sildenafil citrate, or Viagra®, is probably the best known treatment for male erectile dysfunction, boasting that it helps most men achieve harder erections, maintain an erection during sex, can work in as little as 14 minutes, and has a proven safety record. However, because this is a systemic treatment, there is a systemic side effect profile, regardless of how minimal, as well as a delayed time period before reaching therapeutic blood levels. A topical preparation with a similar safety profile that provides immediate, sustained and controlled genital vasodilation would circumvent the aforementioned problems. Furthermore, a topical preparation allows for intimate participation from both parties, offering a richer and more involved sexual experience.

Peripheral Vascular Disease—Peripheral vascular disease (PVD) can be considered a pandemic condition that has the potential to cause loss of limb(s), and even loss of life. PVD manifests as insufficient tissue perfusion caused by existing atherosclerosis that may be acutely compounded by either emboli or thrombi. Many people live daily with PVD; however, in settings such as acute limb ischemia, this disease can be life threatening and can require emergency intervention to minimize morbidity and mortality. Claudication is one of the earliest signs of advancing disease. Claudication occurs because not enough blood is flowing to a muscle. When resting, enough blood flows to the muscle to meet the needs of the muscle. However, walking or exercising, the working muscle needs more blood. A narrowed artery may not let enough through. The primary treatment currently available includes a combination of systemic anticoagulants and lifestyle modifications. Unfortunately, a localized treatment to alleviate the pain from the claudication is not available, and a large percentage of the population is left suffering. A topical preparation which provides sustain release of nitric oxide through the skin could potentially vasodilate the peripheral vasculature, allowing for increased blood flow and resulting in relief.

VII. Discussion

Platforms and methods are presented for generating compositions that provide for controlled and sustained release of nitric oxide. These particles, which combine features of both glassy matrices and hydrogels, are shown to be highly effective in killing the bacterium *Staphylococcous aureus* and the parasite *Plasmodium falciparum*.

Increasing bacterial resistance to current antibiotic treatments has highlighted the need for new and efficacious therapies. The approach described in the present work utilizes sustained release of nitric oxide as the basis for anti-microbial activity. CFU assays of *S. aureus*, treated with increasing concentrations of suspensions of the particulate microgels demonstrated sustained and effective killing. These data indicate that the NO releasing microgels can be used as effective therapeutic agents.

The microparticles provide a facile and versatile delivery system for targeted delivery of therapeutic levels of gNO. The nitrite/sugar based microgel delivery system, aside from ease of preparation, poses significant advantages over earlier NO delivery systems (Bordini el al., 2005; Dobmeier et al., 2004; Nablo et al., 2005). Most significant is that this platform allows for systematic tuning of sustained and controlled delivery of gNO not only through the amount of added nitrite but also though variations in the composition of the gel/glass matrix. The versatile physiochemical nature of the NO microparticles also allows for varying modes of delivery, including percutaneous application, inhalation, local injection and intravenous introduction. The ability both to easily manipulate the polymeric composition and nitrite/sugar content of these particles and to combine them with other synergistic therapeutic agents raises the prospect for a new versatile class of therapeutic agents.

All publications mentioned herein are hereby incorporated in their entirety into the subject application. While the foregoing invention has been described in some detail for purposes of clarity and understanding, it will be appreciated by one skilled in the art, from a reading of the disclosure, that various changes in form and detail can be made without departing from the true scope of the invention in the appended claims.

REFERENCES

Aldin A S, Kinzl L, Eisele R. [Severe complications of *Staphylococcus aureus* infection in the child]. *Unfallchirurg* 104(1) (2001), pp. 85-90.

Alou L, Cafini F, Sevillano D, Unzueta I, Prieto J. In vitro activity of mupirocin and amoxicillin-clavulanate alone and in combination against *staphylococci* including those resistant to methicillin, *International Journal of Antimicrobial Agents*, 23 (5) (2004), pp. 513-516.

Archer G L: *Staphylococcus aureus*: a well-armed pathogen. *Clin Infect Dis* 26(5) (1998), pp. 1179-81.

Baggett H C, Hennessy T W, Rudolph K, et al. Community-onset methicillin-resistant *Staphylococcus aureus* associated with antibiotic use and the cytotoxin Panton-Valentine leukocidin during a furunculosis outbreak in rural Alaska. *J Infect Dis* 189(9) (2004), pp. 1565-73.

Bordini J, Ford P C, Tfouni E. Photochemical release of nitric oxide from a regenerable, sol-gel encapsulated Ru-salen-nitrosyl complex. *Chem Commun (Camb)*. 33 (2005), pp 4169-71.

CDC: Interim guidelines for prevention and control of Staphylococcal infection associated with reduced susceptibility to vancomycin. MMWR Morb Mortal Wkly Rep (1997) 46(27): 626-8, 635.

Costerton J W, Stewart P S. Battling biofilms, *Sci. Am.* 285 (2001), pp. 74-81.

Dobmeier K P, Schoenfisch M H. Antibacterial properties of nitric oxide-releasing sol-gel microarrays. Biomacromolecules. 5(6) (2004), pp 2493-5.

Fang, F. C. Nitric oxide and infection, Kluwer Academic/Plenum Publishers, New York (1999).

Feigen R D, Cherry J D: Coagulase positive staphylococcal infections. In: Feigin R D, Cherry J D, eds. Textbook of Pediatric Infectious Disease. Philadelphia, Pa.: WB Saunders Company; 1998: Chapters 32, 64, 85.

Frank S., Kampfer H., Wetzler C., Pfeilschifter, J. Nitric oxide drives skin repair: novel functions of an established mediator, *Kidney Int.* 61 (2002), pp. 882-888.

Gisby, J and Bryant, J. Efficacy of a new cream formulation of mupirocin: comparison with oral and topical agents in experimental skin infections. *Antimicrob. Agents Chemother.* 44 (2000), pp. 255-260.

Heck D. E., Laskin D. L., Gardne, C. R., Laskin, J. D. Epidermal growth factor suppresses nitric oxide and hydrogen peroxide production by keratinocytes. Potential role for nitric oxide in the regulation of wound healing, *J Biol. Chem.* 267 (1992), pp. 21277-21280.

Ivanova K., Le Poole I. C., Gerzer R., Westerhof W., Das, P. K. Effect of nitric oxide on the adhesion of human melanocytes to extracellular matrix components, *J. Pathol.* 183 (1997), pp. 469-476.

Kloos W E, Bannerman T L: Update on clinical significance of coagulase-negative staphylococci. *Clin Microbiol Rev* 7(1) (1994), pp. 117-40.

Liew, F. Y. and Cox, F. E. Nonspecific defence mechanism: the role of nitric oxide, *Immunol. Today* 12 (1991), pp. A17-A21.

MacMicking J., Xie Q. W., Nathan, C. Nitric oxide and macrophage function, *Annu. Rev. Immunol.* 15 (1997), pp. 323-350.

Nablo B J, Schoenfisch M H. In vitro cytotoxicity of nitric oxide-releasing sol-gel derived materials. Biomaterials. 26(21) (2005), pp 4405-15.

Nouwen J L, Ott A, Kluytmans-Vandenbergh M F. Predicting the *Staphylococcus aureus* nasal carrier state: derivation and validation of a "culture rule". *Clin Infect Dis* 39(6) (2004), pp. 806-11.

Rizk, M., Witte, M. B., Barbul, A. Nitric oxide and wound healing, *World Journal of Surgery* 28 (2004), pp. 301-304.

Robbins M E, Hopper E D, Schoenfisch M H. Synthesis and characterization of nitric oxide-releasing sol-gel microarrays. *Langmuir.* 2004 Nov. 9; 20(23): 10296-302.

Smith T L, Pearson M L, Wilcox K R: Emergence of vancomycin resistance in *Staphylococcus aureus*. Glycopeptide-Intermediate Staphylococcus aureus Working Group. N Engl J Med 340(7) (1999), pp 493-501.

Subczynski, W. K., Wisniewska, A. Physical properties of lipid bilayer membranes: relevance to membrane biological functions, *Acta Biochim. Pol.* 47 (2000), pp. 613-625.

Weller R., Price R. J., Ormerod A. D., Benjamin N., Leifert, C. Antimicrobial effect of acidified nitrite on dermatophyte fungi, Candida and bacterial skin pathogens, *J. Appl. Microbiol.* 90 (2001), pp. 648-652.

von Eiff C, Becker K, Machka K, et al. Nasal carriage as a source of *Staphylococcus aureus* bacteremia. Study Group. *N Engl J Med* 344(1)(2001), pp 11-6.

What is claimed is:

1. A composition for releasing nitric oxide (NO) comprising nitric oxide encapsulated in a matrix of chitosan, polyethylene glycol (PEG), and tetra-methoxy-ortho-silicate (TMOS).

2. The composition of claim 1, wherein nitric oxide is released when the composition is exposed to an aqueous environment.

3. The composition of claim 1, wherein the chitosan is at least 50% deacetylated.

4. The composition of claim 1, wherein the polyethylene glycol has a molecular weight of 200 to 20,000 Daltons.

5. The composition of claim 1, wherein the concentration of chitosan in the composition is 0.05 g-1 g chitosan/100 ml of composition.

6. The composition of claim 1, wherein the concentration of polyethylene glycol (PEG) in the composition is 1-5 ml of PEG/24 ml of composition.

7. The composition of claim 1, wherein the concentration of tetra-methoxy-ortho-silicate (TMOS) in the composition is 0.5 ml-5 ml of TMOS/24 ml of composition.

8. The composition of claim 1, wherein the composition is in the form of particles having a diameter of 0.1 µm to 1,000 µm.

9. The composition of claim 1, wherein the chitosan is at least 80% deacetylated.

10. The composition of claim 1, wherein the chitosan is at least 85% deacetylated.

11. The composition of claim 1, wherein the polyethylene glycol has a molecular weight of 400 Daltons.

12. The composition of claim 1, wherein the composition is in the form of particles having a diameter of 0.09 µm to 100 µm.

13. The composition of claim 1, which further comprises nitrite.

14. The composition of claim 13, wherein the nitrite is a monovalent or divalent cation salt of nitrite.

15. The composition of claim 13, wherein the nitrite is sodium nitrite, calcium nitrite, potassium nitrite, or magnesium nitrite.

16. The composition of claim 13, wherein the concentration of nitrite in the composition is 20 nM to 900 mM.

17. The composition of claim 1, which further comprises reducing sugar.

18. The composition of claim 7, wherein the concentration of reducing sugar in the composition is 20 mg-100 mg reducing sugar/ml of composition.

19. The composition of claim 7, wherein the total concentration of sugar in the composition is 80-120 mg sugar/ml of composition.

20. The composition of claim 7, wherein the reducing sugar is glucose, tagatose, galactose, ribose, fructose, lactose, arabinose, maltose, or maltotriose.

21. The composition of claim 20, wherein the glucose is D-glucose or L-glucose.

22. A composition comprising nitrite, reducing sugar, chitosan, polyethylene glycol (PEG) and tetra-methoxy-orthosilicate (TMOS).

23. The composition of claim 22, wherein the nitrite is a monovalent or divalent cation salt of nitrite.

24. The composition of claim 22, wherein the nitrite is sodium nitrite, calcium nitrite, potassium nitrite, or magnesium nitrite.

25. The composition of claim 22, wherein nitric oxide (NO) is produced in situ in the composition.

26. A method for preparing a composition for releasing nitric oxide (NO), the method comprising:

(a) admixing nitrite, reducing sugar, chitosan, polyethylene glycol (PEG), and tetra-methoxy-ortho-silicate (TMOS);

(b) drying the mixture of step (a) to produce a gel; and (c) heating the gel until the gel is reduced to a powdery solid.

27. A composition for sustained release of nitric oxide produced by the method of claim 26.

28. The method of claim 26, wherein nitric oxide (NO) is produced in situ in the composition.

29. A method for controlling delivery of nitric oxide to a subject comprising applying the composition of claim 1 to the subject.

30. A method of treating an infection in a subject comprising administering to the subject an amount of the composition of claim 1 effective to treat the infection, wherein the infection is a bacterial, viral, fungal or parasitic infection.

31. A method of promoting angiogenesis, vasodilation, wound healing, or hair growth in a subject comprising administering to the subject an amount of the composition of claim 1 effective to promote angiogenesis, vasodilation, wound healing, or hair growth.

32. A method of treating a disorder in a subject comprising administering to the subject an amount of the composition of claim 1 effective to treat the disorder, wherein the disorder is selected from the group consisting of peripheral vascular disease, erectile dysfunction, scleroderma and sickle cell anemia.

* * * * *